United States Patent [19]

Janssens et al.

[11] Patent Number: 5,367,102
[45] Date of Patent: Nov. 22, 1994

[54] PROCESS FOR THE PREPARATION OF 1,1-DICHLORO-1-FLUOROETHANE

[75] Inventors: Francine Janssens, Vilvoorde; James Franklin, Brussels, both of

[73] Assignee: Solvay (Société Anonyme), Brussels,

[21] Appl. No.: 952,495
[22] PCT Filed: Jun. 4, 1991
[86] PCT No.: PCT/BE91/00034
 § 371 Date: Dec. 8, 1992
 § 102(e) Date: Dec. 8, 1992
[87] PCT Pub. No.: WO91/18852
 PCT Pub. Date: Dec. 12, 1991

[30] Foreign Application Priority Data

Jun. 8, 1990 [BE] Belgium .................... 09000579

[51] Int. Cl.⁵ .................................. C07C 17/08
[52] U.S. Cl. .............................. 570/164; 570/177
[58] Field of Search ............. 570/164, 177, 178, 247

[56] References Cited

U.S. PATENT DOCUMENTS

| | | | |
|---|---|---|---|
| 4,329,323 | 5/1982 | Shiozaki et al. | 570/247 |
| 4,948,479 | 8/1990 | Brooks et al. | 204/158.21 |
| 4,968,850 | 11/1990 | Franklin et al. | |

FOREIGN PATENT DOCUMENTS

| | | |
|---|---|---|
| 0361578 | 4/1990 | European Pat. Off. |
| 627773 | 8/1949 | United Kingdom |

OTHER PUBLICATIONS

Journal of Am. Chem. Soc. 1943, pp. 1271–1272; A. L. Henne et al.: "The Addition Of . . . ".

*Primary Examiner*—Alan Sigel
*Attorney, Agent, or Firm*—Spencer, Frank & Schneider

[57] ABSTRACT

The invention relates to a thermal process the production of 1,1-dichloro-1-fluoroethane by hydrofluorination of vinylidene chloride carried out in the absence of any catalyst.

9 Claims, No Drawings

PROCESS FOR THE PREPARATION OF 1,1-DICHLORO-1-FLUOROETHANE

The present invention relates to a process for the production of 1,1-dichloro-1-fluoroethane from 1,1-dichloroethylene, also called vinylidene chloride (VC$_2$), by reaction with hydrogen fluoride in liquid medium in the absence of catalyst(s) and at elevated temperature.

1,1-dichloro-1-fluoroethane is a synthetic product carrying in its molecule, apart from chlorine, fluorine and carbon atoms, hydrogen atoms. The boiling point of this compound is 32° C. under atmospheric pressure. It can be used by itself especially as a blowing agent or in a mixture with other chlorofluorinated hydrogen-containing or hydrogen-free compounds.

The known industrial processes for obtaining 1,1-dichloro-1-fluoroethane all start with 1,1,1-trichloroethane, even though it has been known for a time that this product can be obtained by hydrotiuorination of vinylidene chloride.

Thus, Journal of Am. Chem. Soc. 1943, 65, p. 1272 already describes that the reaction of 1 mol of vinylidone chloride with 4 mol of hydrogen fluoride carried out at 65° C. for 3 hours makes it possible especially obtain 50% of 1,1-dichloro-1-fluoroethane, 5% of 1,1,1-trichloroethane and 15% of tars.

Furthermore, British Patent 627,773 discloses especially the reaction of 8 mol of vinylidene chloride with about 8.7 mol of hydrogen fluoride in the presence of tin chloride at temperatures between 10° C. and 35° C. for 1 hour 45 minutes, as a result of which 1,1-dichloro-1-fluoroethane is obtained at a conversion rate of 32.7%, calculated with respect to the vinylidene chloride used.

However, yields and purities of this kind were not high enough for justifying industrial exploitation, or even a continuation of the studies of the production of 1,1-dichloro-1-fluoroethane by hydrofluorination vinylidene chloride, and consequently this route was abandoned in favour of the one starting with 1,1,1-trichloroethane, which apparently did not have the same disadvantages.

The applicant has now found a process for producing 1,1-dichloro-1-fluoroethane by hydrofluorination of vinylidene chloride which no longer has the drawbacks of the abovementioned processes.

Accordingly, the present invention relates to a process for the production of 1,1-dichloro-1-fluoroetnane by reaction of hydrogen fluoride with vinylidene chloride, in which the reaction is carried out in a liquid medium at a temperature above 70° C. and in the absence of a catalyst.

The hydrogen fluoride necessarily has to be used in the present process in anhydrous form and in a purity of greater than 95% and preferably greater than 99% by volume. It can be introduced into the reactor in gaseous or liquid form.

The vinylidene chloride used must fulfil the same specifications as those described above for hydrogen fluoride, i.e. it has to be anhydrous and pure.

The amounts of hydrogen fluoride and vinylidene chloride, respectively, which are introduced into the reactor, are without any great importance by themselves. In contrast, it is absolutely necessary that the molar ratio in which these two reactants are introduced into the reactor is between 1.5 to 3 mol of HF per 1 mol of vinylidene chloride, if the advantageous results provided by the process of the invention are to be observed.

The reaction mixture in the inside of the hydrofluorination reactor must be maintained in the liquid state for a favourable course of the process of the invention. This can be done by using any known method. A practical method which has given good results consists in operating in a reactor which is maintained under pressure.

The reaction temperature is in general between 75° C. and 130° C. and preferably between 80° C. and 125° C. Under these conditions, the pressure in the reactor is in general between 2 and 30 bar and preferably between 5 and 25 bar.

The selectivity of 1,1-dichloro-1-fluoroethane obtained in the process of the invention is very high and reaches, under operating conditions of 100° C. and for an initial VC$_2$/HF molar ratio of $\frac{1}{2}$, as much as 85% when the conversion rate of VC$_2$ is as high as 98.7%.

When operating according to the process of the invention, the amount of oligomers and tars formed, which are an obstacle to industrial exploitation of the earlier known processes, is very low and can compete with that observed with the processes carried out starting with 1,1,1-trichloroethane.

Thus, when the reaction is carried out at temperatures above 70° C., the total amount of oifgomers observed is less than 5 mol % of the total amount of vinylidene chloride used. It is even possible, by varying the reaction parameters, to obtain amounts of oligomers which are less than 1 mol %, and indeed 0.2 mol %, of the amount of vinylidene chloride used.

Although the process of the invention is carried out in the absence of any catalyst in a purely thermal manner with amounts of reactants and reaction products, such as detailed above, it is obvious that any variant in which a thermal process is used but in which excess reactants, such as vinylidene chloride, hydrogen fluoride, or excess products originating from the reaction, such as hydrogen chloride or 1,[-difluoro-1-chloroethane, are introduced temporarily or continuously in higher or lower amounts than those specified above, are likewise part of the present invention.

The reactors used in the process according to the invention can be made of different materials, such as steel, stainless steel or also different alloys, such as MONEL, INCONEL and HASTELLOY. It is likewise possible to use reactors in which the inside wall is lined with an inert lining, such as a resin layer which is inert under the reaction conditions, such as, for example, fluorinated resins.

The reactors are advantageously equipped with technical devices by means of which the contact between the reactants can be improved. Thus, the reactors can be provided with stirrers, or devices for introducing the reactants can also be provided, thus achieving efficient dispersion of the reactants inside the reaction mixture.

The means of introduction as well as the flow rates of the reactants at the entry of the reactors are regulated in such a manner that the desired proportions of the reactants are maintained inside the liquid reaction medium. Consequently, they are a function especially of the temperature, the filling level of the reactors, the residence time and the discharge rates applied.

Under the conditions described above, the reaction can be operated batchwise or continuously. If it is operated batchwise, the reaction is usually carried out in stirred and sealed autoclaves, and when it is operated continuously, it is preferably carried out in reactors of the mixer type equipped with systems for the continuous introduction of reactants and discharge of products.

No matter what the operating procedure of the reaction, batchwise or continuously, of the process of the invention, it is essential that the discharge means be regulated in such a way that all the hydrogen chloride produced by the process of the invention is substantially removed in gaseous phase, while the other products originating from the reaction or residual products whose boiling temperature is above that of hydrogen chloride are discharged in liquid phase.

If desired, one of the reactants or both can be introduced at a single or at several points spaced around the reactors. Thus, especially several points equipped with means for the introduction of vinylidene chloride into the reactors can be provided, while observing however the molar ratios of the reactants introduced.

The reaction can be carried out in a single reactor or in several reactors connected in series. In this case, it is likewise possible to provide various means for the introduction of the reactants. The two reactants can be introduced into the same reactor or the introduction of one of the reactants can be divided between each of the reactors. It is likewise possible to use several reactors which are fed with each of the reactants, respectively, where the mixtures formed in each of the reactors are circulated in the same direction or in countercurrent.

The method of gas-phase removal of the hydrogen chloride formed by the reaction can be effected by any means known for this purpose. A means which has given good results consists in equipping the reactor with a reflux column. Depending on the efficiency of the reflux applied, the hydrogen chloride additionally contains light organic compounds as byproducts which can, if desired, be removed by conventional means, such as fractional distillation.

The reactors are also advantageously equipped with means for recovering part of the liquid phase. In order to favour the liquid-phase recovery, the reaction is preferably carried out with a reaction medium maintained under a pressure of about 10 to 20 bar.

Finally, the liquid mixture originating from the reactor can then be subjected to separation operations in one or more steps for recovering 1,1-dichloro-1-fluoroethane.

Some of the by-products and impurities can be easily eliminated by distillation. This is for instance the case for 1-chloro-1,1-difluoroethane and 1,1,1-trifluoroethane, as well as for the oligomers formed during the reaction. However, the 1,1-dichloro-1-fluoroethane usually contains impurities such as small quantities of undesired unsaturated chlorinated or chlorofluorinated compounds which can be difficultly separated by distillation, because their boiling points are close to the one of 1,1-dichloro-1-fluoroethane. Indeed, in addition to the unreacted vinylidene chloride, the main unsaturated impurities which may be present in the 1,1-dichloro-1-fluoroethane to be purified are dichloroacetylene, 1,2-dichloro-1-fluoroethylenes (cis and trans isomers), trans 1,2-dichloroethylene traces of 1-chloro-1-fluoroethylene.

The unsaturated chlorinated compounds such as vinylidene chloride, which may still be present in the reaction medium, can be removed by any chemical or physical method known for this. In the particular case vinylidene chloride, the methods which have given good results consist in bromination or chlorination of this compound, followed by separation of the saturated compounds obtained by distillation.

If it is desired to recover the 1,1-dichloro-1-fluoroethane with a purity of greater than 99% volume, a procedure which has given good results consists in:

first subjecting the organic liquid phase originating from the hydrofluorination reactor and previously separated from the liquid phase containing the inorganics, i.e. substantially hydrogen fluoride, to distillation so as to remove, in gaseous phase, the products whose boiling point is below that of 1,1-dichloro-1-fluoroethane, i.e. substantially in order to eliminate traces of 1-chloro-1,1-difluoroethane and 1,1,1-trifluoroethane, subjecting the liquid phase originating from the preceding distillation to a chlorination operation so as to chlorinate the unsaturated products, such as vinylidene chloride remaining in the medium and finally, removing the chlorinated products formed in the previous step by distillation.

However, if it is easy to eliminate the vinylidene chloride and the dichloroacetylene by any suitable method, this is not necessarily the case the unsaturated chlorinated compounds and more particularly for the cis and trans 1,2-dichloro-1-fluoroethylenes which are significantly less reactive. When the chlorination treatment is effected under more severe conditions to also chlorinate these less reactive unsaturated chlorinated compounds, a rather important amount 1,1-dichloro-1-fluoroethane may also react, inducing the formation of 1,1,2-trichloro-1-fluoroethane. This loss of output in 1,1-dichloro-1-fluoroethane has been noticed in all the tests effected under more drastic conditions, even by photochemical chlorination as in the presence of a Lewis acid.

Furthermore, the elimination of the cis and trans 1,2-dichloro-1-fluoroethylenes appears to be more difficult as it has been observed that, in some cases, after passing through a minimum, their concentration grows if the chlorination treatment is extended.

A possible explanation for this phenomenon would be their formation by dehydrochlorination of 1,2,2-trichloro-1-fluoroethane produced at the expense of the 1,1-dichloro-1-fluoroethane. The Applicant however does not intend to be bound by this explanation.

On the other hand, it has been further observed that the 1,1-dichloro-1-fluoroethane may undergo an important degradation downstream of the chlorination stage of the unsaturated impurities, namely in the following distillation stages, when the chlorination is effected in the presence of equal or greater amounts about 10 ppm of Lewis acids or when there remains, after the chlorination reactor, equal or greater amounts about 10 ppm of Lewis acids and especially $FeCl_3$. The chlorination reactor, as well as all the equipment downstream, are therefore preferably realized with corrosion resistant materials, such as MONEL, INCONEL and HASTELLOY, which are not likely to introduce in the medium between the chlorination stage and the end of the purification amounts of $FeCl_3$ greater than or equal to 10 ppm.

In a preferred embodiment of the process according to the invention, these disadvantages may be obviated while enabling the almost complete transformation of all the unsaturated chlorinated or chlorofluorinated impurities, by chlorinating these impurities in order to obtain products having boiling points which are sufficiently different from the boiling point of 1,1-dichloro-1-fluoroethane so as to be easily separated afterwards by distillation.

In order to do this, the chlorination may be effected by reacting the liquid medium to be treated with an excess of chlorine, in the presence of very small amounts of a Lewis acid and preferably FeCl$_3$, at a temperature, adjusted in function of the amount of FeCl$_3$, sufficiently high to enable the almost complete elimination of the impurities in a reasonable lapse of time, not exceeding a few hours, but sufficiently low to avoid the chlorination of a part of the 1,1-dichloro-1-fluoroethane.

In a most preferred embodiment, before the chlorination stage, the 1,1-dichloro-1-fluoroethane is freed from products having a boiling point higher than that of the 1,1-dichloro-1-fluoroethane, i.e. essentially the oligomers and tars. This separation may be effected by conventional distillation.

The amount of FeCl$_3$ used in the chlorination of this preferred embodiment of the invention, is necessarily lower than 10 ppm. Preferably, this amount is lower than or equal to about 6 ppm. Although FeCl$_3$ is used in small amounts, its presence is however absolutely required to effect the chlorination of all the unsaturated impurities. The minimal amount of FeCl$_3$ enabling a chlorination of the unsaturated impurities in a reasonable time is about 0,05 ppm. Preferably the amount of FeCl$_3$ is greater than or equal to 1 ppm. Most preferrably, it is about 3 ppm.

Owing to the low amounts of FeCl$_3$ used, the process of the invention has in addition the advantage to avoid a tedious and delicate stage of elimination of FeCl$_3$ from the medium by alcaline washing or by complexation, previously to any further treatment, stage which is absolutely necessary to avoid altering the purity of the 1,1-dichloro-1-fluoroethane when the chlorination effected in the presence of more important amounts FeCl$_3$.

In practice, the FeCl$_3$ may be introduced in the chlorinator by different means. A means which has given good results consists in saturating a fraction of the flow of 1,1-dichloro-1-fluoroethane to be purified by FeCl$_3$. By way of example, the solubility of FeCl$_3$ in 1,1-dichloro-1-fluoroethane at room temperature is about 7 ppm. Other solvents, capable of dissolving a sufficient amount of FeCl$_3$, which are inert in the chlorination conditions and easily recovered in a further separation stage, may also be used as far as it is understood that they are used in such amounts that the total amount of FeCl$_3$ present in the reaction medium is not in excess of the values cited herebefore. Solvents corresponding to these criteria are for instance tetrachloromethane, trichloromethane and 1,2-dichloroethane.

With the amounts of FeCl$_3$ defined hereabove in the medium, a temperature of about 75° C. already enables to effect the chlorination of the unsaturated impurities at a sufficient rate so as to enable an industrial application. A suitable chlorination rate is obtained when the temperature is greater than or equal to about 80° C. However, at temperatures greater than about 120 ° C., the transformation of 1,1-dichloro-1-fluoroethane 1,1,2-trichloro-1-fluoroethane reaches important amounts of Preferably, the chlorination is effected at a temperature lower than or equal to about 110° C.

Chlorine is introduced in an amount in excess with respect to the impurities to be chlorinated. The molar ratio between the chlorine and the sum of the unsaturated impurities to be chlorinated may be varied within large ratios. A ratio greater than or equal to about 10 enables to reach an acceptable reaction rate; this ratio may also be much larger without therefore cause the degradation of 1,1-dichloro-1-fluoroethane. This ratio in general does not exceed 100.

The chlorination may be effected at atmospheric pressure or at higher pressures. This pressure mall be either the autogeneous pressure, or a nigher pressure, induced by the introduction of an inert gas, e.g. nitrogen. Usually, the chlorination treatment is effected at a pressure of about 4 bar to about 15 bar.

Under the conditions defined above, an almost complete chlorination of the unsaturated chlorinated and chlorofluorinated compounds is obtained with a treatment time of 1,1-dichloro-1-fluoroethane to be purified in the chlorinator varying from a few minutes to about 2 hours. On an industrial basis, the residence time of the 1,1-dichloro-1-fluoroethane in the chlorinator is of course adjusted in function of the required purity. Classically, a satisfactory purity is obtained with a residence time of 10 to 60 minutes.

Examples 1 to 4 are given to illustrate the invention. Example 5 is given as a comparison.

EXAMPLE 1

Vinylidene chloride is first introduced with stirring into a cylindrical stainless steel 316 reactor (autoclave) of 0.5 litre which is equipped with a stirrer, cooled to −30° C. and put under a vacuum 15 mbar, and allowed to adopt the temperature of the reactor for a few minutes so as to obtain a drop in pressure in the autoclave.

Hydrogen fluoride which is maintained at ambient temperature in a stainless steel 316 cylinder is then introduced into the reactor by suction.

The reactor is then immersed in a thermostat preheated to the desired temperature, and the pressure is regulated at a desired value, which is a function of the experimental temperature, in such a manner that only hydrogen chloride and the organic products which are lighter than 1,1-dichloro-1-fluoroethane, i.e. substantially 1-chloro-1,1-difluoroethane and possibly 1,1,1-trifluoroethane, are allowed to escape from the reactor.

The moment at which the reactor is immersed in the preheated thermostat determines the beginning of the reaction.

During the entire course of the reaction, the development of the pressure in the reactor is monitored while keeping the temperature constant.

The gaseous effluent is collected and measured in a water meter after neutralisation and destruction of the discharged hydrochloric acid and hydrofluoric acid in a scrubber containing a dilute NaOH solution.

After the desired reaction time, the reactor is finally abruptly cooled to 0° C. by means of a cooling bath, and the liquid and gaseous phases are removed from the reactor (via an NaOH gas-washing bottle connected to the gas meter) and analysed.

Under the general conditions described above, three batchwise experiments were carried out at temperatures respectively of 75° C. (experiment 1), 100° C. (experiment 2) and 125° C. (experiment 3), the parameters and results of which are listed below.

| Experiment 1 | |
|---|---|
| Temperature of the experiment | 75° C. |
| HF/VC$_2$ molar ratio used | 2 mol/mol |

-continued

| | |
|---|---|
| Amount of VC$_2$ used | 250 g |
| Amount of HF used | 103 g |
| *Results in mol % after 5 h of reaction: | |
| Conversion rate of VC$_2$ | 98.7% |
| Selectivity of 1,1-dichloro-1-fluoroethane | 88% |
| Byproducts: | |
| 1-chloro-1,1-difluoroethane | 4% |
| 1,1,1-trifluoroethane | 3.3% |
| total oligomers | 4.7% |
| | (expressed as converted VC$_2$) |

Experiment 2

| | |
|---|---|
| Temperature of the experiment | 100° C. |
| HF/VC$_2$ molar ratio used | 2 mol/mol |
| Amount of VC$_2$ used | 250 g |
| Amount of HF used | 103 g |
| *Results in mol % after 2 h 30 min of reaction: | |
| Conversion rate of VC$_2$ | 98.7% |
| Selectivity of 1,1-dichloro-1-fluoroethane | 83.5% |
| Byproducts: | |
| 1-chloro-1,1-difluoroethane | 10% |
| 1,1,1-trifluoroethane | 3% |
| total oligomers | 2.5% |
| | (expressed as converted VC$_2$) |

Experiment 3

| | |
|---|---|
| Temperature of the experiment | 125° C. |
| HF/VC$_2$ molar ratio used | 2 mol/mol |
| Amount of VC$_2$ used | 250 g |
| Amount of HF used | 103 g |
| *Results in mol % after 3 h 30 min of reaction: | |
| Conversion rate of VC$_2$ | 99.3% |
| Selectivity of 1,1-dichloro-1-fluoroethane | 78% |
| Byproducts: | |
| 1-chloro-1,1-difluoroethane | 16% |
| 1,1,1-trifluoroethane | 4% |
| total oligomers | 1% |
| | (expressed as converted VC$_2$) |

* = these results are obtained by GPC (gas phase chromatography) analysis by recovering all the organic compounds present in the gaseous phase and the liquid phase of the reactor.

Thus, it can be seen from the batchwise results that hydrofluorination of VC$_2$ at high temperature without catalyst(s) enables high conversion rates of VC$_2$ to be obtained, which are close to 100% while the selectivities of 1,1-dichloro-1-fluoroethane observed are around 80%, or even 90%.

EXAMPLE 2

52 g/h of HF and 138 g/h of VC$_2$, i.e. a HF/VC$_2$ molar ratio of 1.7 mol/mol at the reactor inlet, are introduced continuously into a stainless steel 316 stirred double-jacketed reactor of 200 cm$^3$, which heated to 120° C. by circulation of oil and overflows into a discharge tube maintained at the same temperature the reactor.

The pressure in this reactor is controlled at 18 bar so as to maintain the liquid reaction medium at 120° C.

After being kept in operation for 4 hours, samples of the gaseous phase and the liquid phase overflowing from the autoclave are taken.

After letdown to atmospheric pressure, the effluent is neutralised in a scrubber containing dilute caustic lye (1/10 molar), and the gases then pass into a wet meter via a sampling system composed of two pyrex ampoules of 100 cm$^3$, for measuring the throughput. traction of the aqueous phase from the scrubber with carbon tetrachloride is also carried out in order to obtain complete analysis of all the organic compounds present and formed in the reactor.

The organic products are then analysed as Example 1 by gas-phase chromatography, the unconsumed HF is measured by ionometry by means of a specific electrode sensitive to F$^-$ ions, and the HCl formed is measured by potentiometry using silver nitrate.

The operating conditions and results obtained under these conditions are listed in the table below.

TABLE

| | | |
|---|---|---|
| Temperature | °C. | 120 |
| Pressure | bar | 18 |
| Residence time | hours | 1 |
| Stirrer speed | rpm | 400 |
| HF throughput | g/h | 52 |
| VC$_2$ throughput | g/h | 138 |
| HF/VC$_2$ ratio | mol/mol | 1.7 |
| Conversion rate of VC$_2$ | % | 94.1 |
| Selectivities of: | | |
| 1,1-dichloro-1-fluoroethane | % | 91.2 |
| 1-chloro-1,1-difluoroethane | % | 6.3 |
| 1,1,1-trifluoroethane | % | 0.6 |
| 1,1,1-trichloroethane | % | 1.6 |
| total oligomers | % | 0.2 |
| | | (expressed as converted VC$_2$) |

From the results of this Example 2 in which the hydrofluorination reaction of VC$_2$ is conducted continuously it can be deduced that the yields and selectivities can still be improved compared with the excellent results already observed in Example 1, where experiments carried out in a batchwise procedure are reproduced.

EXAMPLE 3

The organic phase of a preparation unit of 1,1-dichloro-1-fluoroethane (97 % by weight of 1,1-dichloro-1-fluoroethane), freed by distillation from the by-products which are more volatile and heavier than the 1,1-dichloro-1-fluoroethane, is introduced in a reactor made of MONEL operating continuously. Simultaneously, FeCl$_3$ is introduced in the reactor in such a ratio that in the chlorinator, the organic phase contains 0.6 ppm of FeCl$_3$ and 80 g of chlorine per liter of organic phase. The chlorination reactor is maintained at a temperature of 100 ° C.±3° C. The pressure is adjusted at 9 bar by means of nitrogen. The residence time of the organic phase in the reactor is 1 hour. Table II shows the initial and final contents of unsaturated chlorinated and chlorofluorinated compounds.

TABLE II

| | Contents at the inlet of the chlorinator (ppm) | Contents at the outlet of the chlorinator (ppm) |
|---|---|---|
| vinylidene chloride | 593 | <5 |
| dichloroacetylene | 173 | <1 |
| 1,2-dichloro-fluoroethylene(cis) | 77 | 8 |
| 1,2-dichloro-fluoroethylene (trans) | 41 | <5 |
| 1,2-dichloro-ethylene (trans) | 392 | <5 |
| 1-chloro-1-fluoroethylene | 5 | 2 |

EXAMPLE 4

The organic phase of a preparation unit of 1,1-dichloro-1-fluoroethane (97% by weight of 1,1-dichloro-1-fluoroethane), freed by distillation from the by-products which are more volatile and heavier than the 1,1-dichloro-1-fluoroethane, is introduced in a reactor made of MONEL operating continuously. In the reactor are also introduced FeCl₃ in such a ratio that, in the chlorinator, the organic phase contains 3 ppm of FeCl₃ and 80 g of chlorine per liter of organic phase.

The chlorination reactor is maintained at a temperature of 80° C.±3° C.

The pressure is adjusted at 9 bar by means of nitrogen. The residence time of the organic phase in the reactor is 45 minutes. Table III shows the initial and final contents of the main unsaturated chlorinated and chlorofluorinated compounds

TABLE III

|  | Contents at the inlet of the chlorinator (ppm) | Contents at the outlet of the chlorinator (ppm) |
| --- | --- | --- |
| vinylidene chloride | 431 | <5 |
| dichloro- acetylene | 17 | <1 |
| 1,2-dichloro- fluoroethylene(cis) | 38 | <5 |
| 1,2-dichloro- fluoroethylene (trans) | 43 | <5 |

EXAMPLE 5 (COMPARISON)

The organic phase of a preparation unit of 1,1-dichloro-1-fluoroethane (97% by weight of 1,1-dichloro-1-fluoroethane), freed by distillation from the by-products which are more volatile and heavier than the 1,1-dichloro-1-fluoroethane, is introduced in a reactor made of MONEL operating continuously. In the reactor are also introduced FeCl₃ in such a ratio that, in the chlorinator, the organic phase contains 40 ppm of FeCl₃ and 80 g of chlorine per liter of organic phase.

The chlorination reactor is maintained at a temperature of 80° C.±3° C. The pressure is adjusted at 9 bar by means of nitrogen. The residence time of the organic phase in the reactor is 45 minutes. Table IV shows the initial and final contents of the main unsaturated chlorinated and chlorofluorinated compounds.

TABLE IV

|  | Contents at the inlet of the chlorinator (ppm) | Contents at the outlet of the chlorinator (ppm) |
| --- | --- | --- |
| vinylidene chloride | 525 | <5 |
| dichloro- acetylene | 28 | <1 |
| 1,2-dichloro- fluoroethylene(cis) | 41 | 20 |
| 1,2-dichloro- fluoroethylene (trans) | 12 | 10 |

The comparison of the results described in Tables III and IV enables to establish the extremely important influence of low amounts of FeCl₃ (Table III) on the elimination of impurities of the types cis and trans 1,2-dichlorofluoroethylene and hence on the purity of the 1,1-dichloro-1-fluoroethane finally obtained.

We claim:

1. A process for the preparation of 1,1-dichloro-1-fluoroethane, comprising:

reacting hydrogen fluoride and vinylidene chloride in a liquid medium at a molar ratio of hydrogen fluoride to vinylidene chloride of between 1.5 to 3 mol/mol at a temperature above 70° C. in the absence of catalysts to produce 1,1-dichloro-1-fluoroethane; and recovering said 1,1-dichloro-1-fluoroethane.

2. The process according to claim 1, wherein the temperature of the liquid medium is between 75° C. and 130° C.

3. The process according to claim 2, wherein the temperature is between 85° C. and 125° C.

4. The process according to claim 1, wherein the reaction is carried out under autogenous pressure.

5. The process according to claim 4, wherein the pressure is between 2 and 30 bar.

6. The process according to claim 1, wherein the residual vinylidene chloride is brominated or chlorinated.

7. A process for the preparation of 1,1-dichloro-1-fluoroethane having a purity of greater than 99% by volume, comprising:

reacting hydrogen fluoride and vinylidene chloride at a molar ratio of hydrogen fluoride to vinylidene chloride of between 1.5 to 3 mol/mol at a temperature above 70° C. in the absence of any catalyst, distilling the organic phase obtained, chlorinating the liquid phase originating from this distillation operation, said liquid phase comprising 1,1-dichloro-1-fluoroethane and unsaturated impurities, said chlorination effected by treating said unsaturated impurities with an excess of chlorine, in the presence of about 0.05 to 10 ppm of FeCl₃, and removing the chlorination products obtained after said chlorination by another distillation.

8. Process according to claim 7, wherein the chlorination treatment is effected in the presence of 0.05 to 6 ppm of FeCl₃, at a temperature of 75° to 120° C.

9. Process according to claim 7, wherein, previously to the chlorination treatment, the organic phase is submitted to two distillation treatments, the first one to eliminate the products with a boiling point lower than the boiling point of 1,1-dichloro-1-fluoroethane, and the other one to eliminate the products with a boiling point higher than the boiling point of the 1,1-dichloro-1-fluoroethane.

* * * * *